Figure 1:
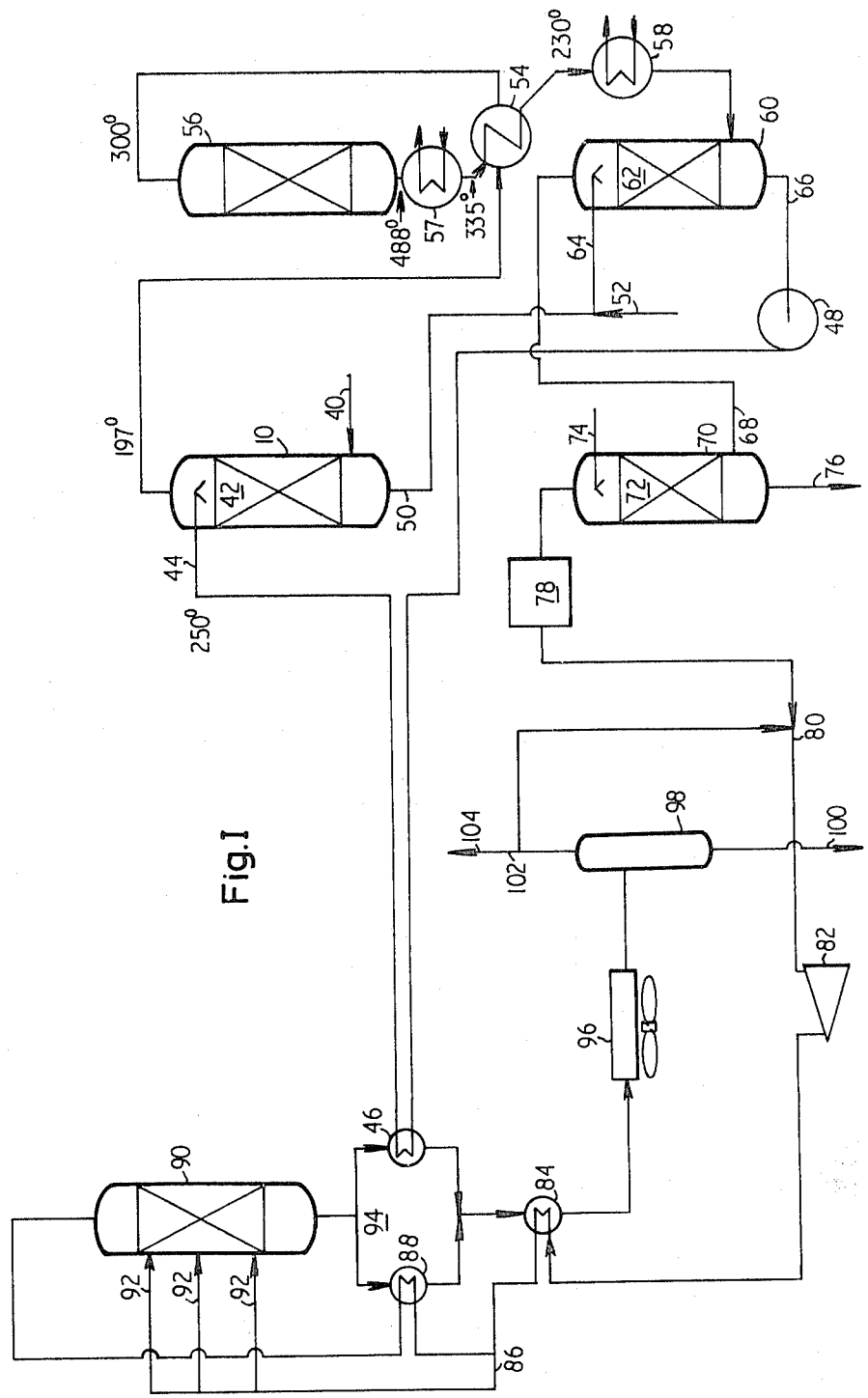

United States Patent [19]

Pinto

[11] 4,235,800

[45] Nov. 25, 1980

[54] SYNTHESIS GAS

[75] Inventor: Alwyn Pinto, Norton, England

[73] Assignee: Imperial Chemical Industries Limited, London, England

[21] Appl. No.: 40,311

[22] Filed: May 18, 1979

[30] Foreign Application Priority Data

May 31, 1978 [GB] United Kingdom ............... 25657/78

[51] Int. Cl.$^3$ .............................................. C07C 29/15
[52] U.S. Cl. .................................... 260/449.5; 252/373
[58] Field of Search ..................... 260/449.5; 423/655, 423/656; 252/373

[56] References Cited

U.S. PATENT DOCUMENTS

| | | | |
|---|---|---|---|
| 3,850,840 | 11/1974 | Aldridge et al. | 423/655 |
| 4,065,483 | 12/1977 | Pinto | 260/449.5 |
| 4,072,625 | 2/1978 | Pinto | 252/373 |

FOREIGN PATENT DOCUMENTS

| | | | |
|---|---|---|---|
| 1142781 | 2/1969 | United Kingdom | 260/449.5 |
| 1309872 | 3/1973 | United Kingdom | 260/449.5 |
| 1484366 | 9/1977 | United Kingdom | 260/449.5 |

OTHER PUBLICATIONS

Staege, Erdoel-Erdgas-Zeitschrift 92, 381–387, 1976.
Mehta, Hydrocarbon Processing, May, 1976, 165–168.

*Primary Examiner*—Howard T. Mars
*Attorney, Agent, or Firm*—Cushman, Darby & Cushman

[57] ABSTRACT

Methanol is produced from a carbon monoxide stream by reacting carbon monoxide with steam in a catalytic shift reaction, removing any excess steam and at least part of the carbon dioxide from the shifted gas, reacting the resulting gas over a copper-containing methanol synthesis catalyst at under 300° C., heat exchanging reacted synthesis gas with water under pressure and bringing the resulting hot water into direct heat exchange with the carbon monoxide stream to provide steam for the shift reaction. In a preferred process the carbon monoxide stream is freed of non-refractory sulphur compounds before the shift stage and the refractory sulphur compounds are converted in the shift stage to $H_2S$, which is removed with the carbon dioxide.

9 Claims, 3 Drawing Figures

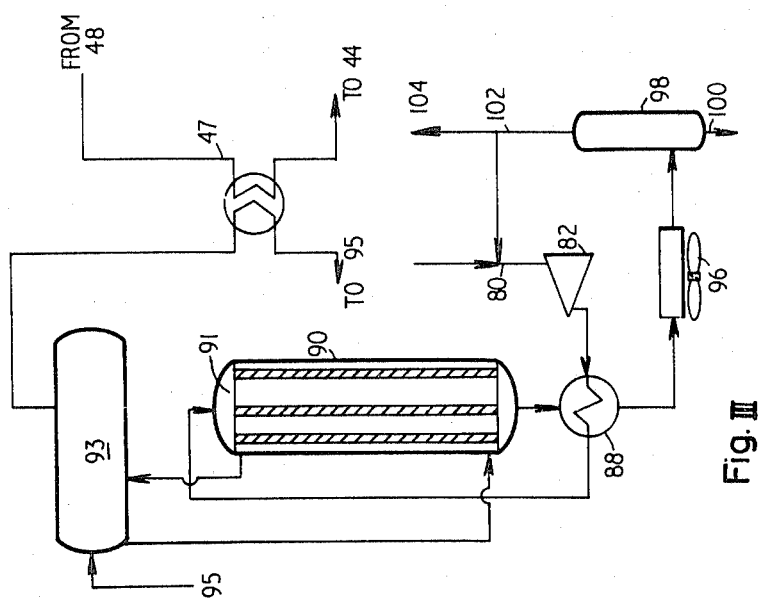
Fig. III
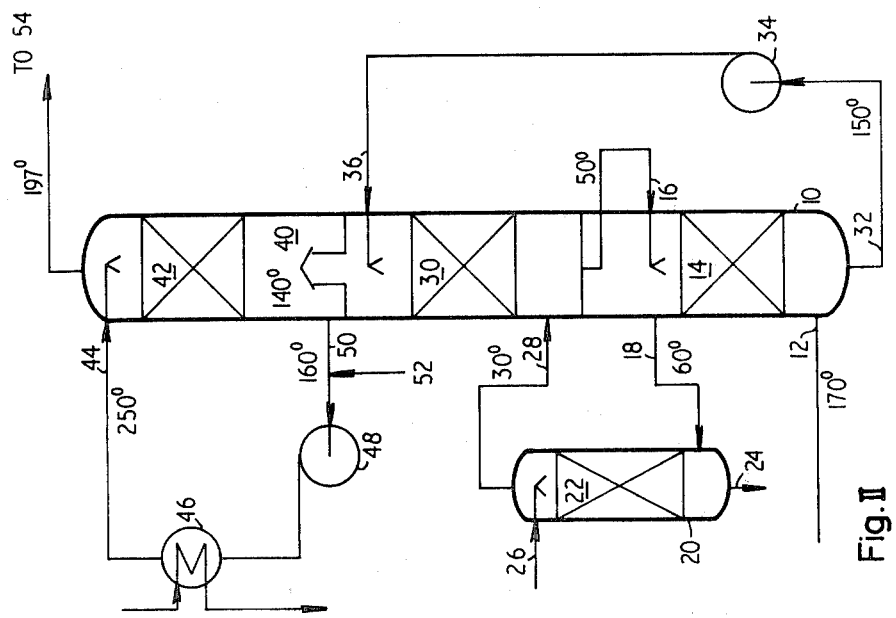
Fig. II

SYNTHESIS GAS

SYNTHESIS GAS

This invention relates to synthesis gas and in particular to the production of methanol synthesis gas and methanol from a carbon monoxide stream.

Carbon monoxide streams, such as metallurgical off-gases or gases made by non-catalytic partial oxidation of carbonaceous feedstocks have to be subjected to the shift reaction $$CO + H_2O \rightarrow CO_2 + H_2$$

followed by partial $CO_2$-removal in order to produce a methanol synthesis gas containing hydrogen and carbon oxides in the required ratio R, where $R = (H_2 - CO_2) \div (CO + CO_2)$. R is usually in the range 2 to 3, although lower ratios, for example down to 1.5, have been proposed and higher ratios, especially up to about 4, have been used. A typical prior process for making methanol synthesis gas from a carbon monoxide stream is described in the article by Staege in Erdoel-Erdgas-Zeitschrift 1976, 92, 381-387.

We have devised a process by which the steam required for this process can be at least partly provided by utilising the exothermic heat of the methanol synthesis reaction.

According to the invention a process for producing methanol from a carbon monoxide stream comprises the steps of (a) forming a gaseous mixture comprising carbon monoxide and steam;

(b) reacting the mixture over a shift catalyst to produce a shifted gas comprising carbon monoxide, carbon dioxide and hydrogen;

(c) removing any excess steam and at least part of the carbon dioxide from the shifted gas;

(d) reacting the resulting gas over a copper-containing methanol synthesis catalyst at an outlet temperature under 300° C.; and (e) cooling the reacted synthesis gas and separating methanol from it: and is characterised by the steps of (i) in step (e) transferring exothermic heat of synthesis into water under pressure; and (ii) in step (a) bringing the resulting hot water under pressure into direct heat exchange with the carbon monoxide stream, whereby to supply at least part of the steam of the gaseous mixture.

The carbon monoxide stream can be a by-product such as the off-gas from a basic oxygen steelmaking furnace but more conveniently the product of partial oxidation of a carbonaceous feed-stock such as a gaseous hydrocarbon, volatilisable hydrocarbon, heavy oils such as crude oil or residual oils, solids such as coal, coke and shales and waste materials such as polymers and wood products. The pressure of the stream is preferably at least 10 bar abs. especially in the range 20–120 bar abs. and thus the process of the invention is preferably operated in combination with a preceding step of partial oxidation itself operated at a pressure high enough to produce the stream without compression. Suitable processes include those known by the names of Shell, Texaco, Lurgi and Koppers-Totzek (new).

The carbon monoxide stream suitably contains 20 to 70% v/v of carbon monoxide and, as made by partial oxidation, commonly contains 10 to 50% v/v of hydrogen and 2 to 30% of carbon dioxide, and also 0.1 to 5% v/v of sulphur compounds calculated as equivalent hydrogen sulphide $H_2S$.

The combination process normally includes one or more purification steps applied to the carbon monoxide stream before step (a). These are, in particular:

removal of by-product carbon, usually by water-scrubbing and often with transfer of carbon to a hydrocarbon for recycle to the partial oxidation;

scrubbing with an absorbent liquid, to remove at least $CO_2$ and $H_2S$ and possibly other sulphur compounds. There may also be a step of catalytic removal of nitrogen oxides and/or hydrogen cyanide.

Two general classes of absorbent-scrubbing process are available. In one, exemplified by Lurgi's "Rectisol" using methanol, $CO_2$, $H_2S$ and refractory sulphur compounds such as COS can be very thoroughly removed and do not affect the design of the subsequent shift step. Such a process, however, requires the gas to be cooled to $-10°$ to $-40°$ C., which usually entails an initial stage of methanol treatment to remove water before the cold removal of sulphur compounds. The other class, using absorbents such as the chemical and physical solvents (other than methanol) set out below, can remove $CO_2$ and $H_2S$ efficiently but not the refractory sulphur compounds. They have the advantage, however, of being operable at temperatures in the range $-10°$ to $100°$ C. and are therefore preferred. The refractory sulphur compounds decomposed with are thereafter decomposed in shift stage (b) with formation of $H_2S$ and the $H_2S$ is removed in stage (c) along with the $CO_2$.

Entering the direct heat exchange in step (ii) the carbon monoxide stream is suitably at a temperature in the range $100°$-$180°$ C. Part or all of the heat required to bring it to this temperature is provided preferably by contacting the stream with warm water. When the source of the stream is a partial oxidation with water-scrubbing, the stream is delivered from the water-scrubbing typically at $150°$-$200°$ C. and saturated with water vapour. It is conveniently cooled to or towards the temperature of the absorbent-scrubbing by contacting it with water at $0°$-$100°$ C. and the resulting warm water is used to re-heat the absorbent-scrubbed stream to $100°$-$180°$ C. After such contacting the stream typically contains 2 to 15% v/v of water vapour and is ready for the direct heat exchange in step (ii) in which its temperature and steam content are increased.

The hot water from step (i) is suitably at a temperature in the range $200°$ to $270°$ C. In the product of step (ii) the molar ratio of steam to dry gas is suitably in the range 0.2 to 0.5, and the gas temperature is typically in the range $180°$-$230°$ C., so that further heating is required before the shift stage.

The shift catalyst preferably contains compounds of one or more metals from Group VIII of the Periodic Table. If the sulphur content of the carbon monoxide stream is not too high, for example up to 1000 ppm v/v calculated an equivalent $H_2S$, iron-chrome can be used. At any sulphur content greater than about 100 ppm v/v as $H_2S$ a cobalt molybdenum sulphide type catalyst can be used. If the sulphur content is very low, as in gas purified by cold methanol, a copper-containing catalyst can be used.

The shift outlet temperature is preferably in the range $350°$ to $500°$ C. and thus an iron-chrome or cobalt molybdenum type catalyst is preferably used. As a result the shifted gas can be cooled with generation of steam at a pressure in the range 50 to 150 bar abs. The over-all effect of the process of the invention is that the heat in the reacted methanol synthesis gas at under 300° C., by heat exchange with which it is not practicable to generate steam at over about 40 bar abs. pressure, is upgraded to a higher level. The steam generated by cooling the shifted gas can be at the same pressure as that generated in waste heat boilers in a preceding partial oxidation step, and a common steam drum can be used.

Other heat exchanges in the shift outlet gas stream include feed preheating by indirect heat exchange and steam removal. Feed preheating uses little heat as a result of the relatively high temperature, typically 180° to 230° C., following the direct heat exchange in step (ii). Steam removal is preferably by direct heat exchange with water and the resulting warm water can be used as feed for the heat exchange with reacted methanol synthesis gas in step (i).

Removal of carbon dioxide is effected after steam removal. For this purpose the so-called "chemical" solvents can be used, such as ethanolamines or potassium carbonate, especially in the established processes such as "Amine Guard", "Benfield", "Benfield-DEA", "Vetrocoke" and "Catacarb", at any of the pressures contemplated for the process of the process of the invention.

For effective use of physical solvents the process pressure is preferably at least 20, especially at least 40, bar abs.; however, since synthesis gas to be used over a copper-containing catalyst preferably contains 1–15, especially 2–10% v/v of carbon dioxide, the pressure need not be as high as in the production of ammonia synthesis gas in which substantially complete removal of carbon dioxide is needed.

As examples of physical solvents there may be mentioned:
tetramethylene sulfone ("Sulfinol")
propylene carbonate (Fluor)
N-methyl-2-pyrrolidone ("Purisol")
dimethyl ether of polyethyleneglycol ("Selexol")
methanol ("Reactisol")

Whichever solvent is used, it removes $H_2S$ at the same time as $CO_2$. Of these, only methanol removes COS thoroughly.

A variety of general types of methanol synthesis processes have been proposed, differing in the methods adopted for handling the heat evolved in the synthesis reaction. Any one or more of these can be used excepting, of course, those designed to use directly all the relatively low pressure ("intermediate pressure") steam generated by heat exchange with the reacting gas or reacted gas in the synthesis. Thus synthesis may be over a catalyst in tubes surrounded by a coolant or in the space around tubes containing coolant. The coolant may be for example pressurised water or a mixture of diphenyl and diphenyl ether; the pressurised water can be used as feed for step (i) directly or, like the mixture, heat-exchanged in liquid form with suitable water to be fed to step (i). Alternatively the coolant water may be allowed to boil and the resulting intermediate pressure steam condensed in heat exchange with the water to be fed to step (i). In another process the catalyst bed can be in several parts with heat-abstraction by coolant between the parts. In a third process the catalyst temperature can be controlled by heat exchange with cool feed gas passing through tubes in the catalyst bed or through the space surrounding catalyst-filled tubes. For the first two of such processes reactors not much simpler than previously proposed steam-raising processes are required, however, and it may therefore be preferred to use the third or, better still, a process in which the temperature is controlled by injecting cool synthesis gas ("quench gas") into the hot reacting synthesis gas. Quench gas can be injected into mixing chambers between successive parts of a catalyst bed or successive reactor vessels. A very convenient system involves a single body of catalyst in which are disposed catalyst-free perforated hollow bars each having a sparger for introducing the quench gas, the bars being large enough in cross section for their interiors to constitute mixing zones and close enough together or to the catalyst bed walls to cause a substantial proportion of reaction mixture to pass through their interiors, as described in our U.K. specification No. 1,105,614. The temperature of quench gas can be below 50° C., but thermal efficiency is better if it is at between 50° and 150° C.

The volume space velocity of the flow of gas through the synthesis catalyst bed is typically in the range 5000–50,000 hour$^{-1}$ and is preferably fixed at a level such that the gas leaves the catalyst bed when the quantity of methanol formed has been sufficient to raise the gas temperature to the design level, which is under 300° C. and most preferably under 280° C. The methanol content of the reacted gas is for example 2–5% for a process at 50 bar abs and proportionately more at higher pressures. Consequently unreacted carbon oxides and hydrogen are left over after methanol has been recovered and are preferably passed again over a methanol synthesis catalyst, for example, by recirculation to the inlet of the catalyst and mixing with fresh synthesis gas. The above space velocity range refers to the mixture in such a process.

In a preferred way of transferring to the feed water for step (i) the heat evolved in the synthesis, reacted gas leaving the catalyst is passed through two parallel heat exchanges, the first of which heats synthesis gas to synthesis inlet temperature, which is preferably 20°–40° C. lower than the outlet temperature of the catalyst bed. The second heats water to a temperature preferably in the range 200°–270° C. under a pressure too high to permit boiling to take place or heats a coolant (such as described above) from which heat is to be transferred to such water. The reacted gas becomes cooled initially to 150°–190° C. in these exchangers. Preferably it is then (suitably after re-uniting the two streams) heat-exchanged with cold synthesis gas from the generation section or methanol recovery or both. This affords a useful secondary heat recovery and decreases the capacity required of the first heat exchanger. After secondary heat recovery the gas is passed to a cooler and separator for recovery of methanol.

In the alternative way of transferring heat to the feed water, by raising steam in the reactor and condensing it in heat exchange with the feed water, the reacted gas leaving the reactor can be cooled to 50°–150° C. in a single heat exchange with cold synthesis gas and then passed to the cooler and separator.

Unreacted gas from the separator is preferably recirculated but, if the fresh synthesis gas has a hydrogen to carbon oxides ratio different from stoichiometric and/or contains non-reactive gases such as nitrogen, methane or argon, it is necessary to purge a part of it in order to prevent the concentration of such gases from building up too much in the gas passing over the catalyst. Since the purge gas is at only slightly under synthesis pressure, a useful energy recovery results from letting it down in an expansion engine. Since the purge gas is at the low temperature of methanol separation, it is capable of absorbing low-grade heat from other process streams in the plant and thus the energy recovery from purge gas is yet more valuable. After letting-down the purge gas can be used as a fuel or source of hydrogen for purposes such as feedstock desulphurisation.

Although the invention resides essentially in transferring the heat evolved in methanol synthesis to water without boiling it, it is within the invention to conduct part of the synthesis so as to raise steam directly. It is also within the invention to use part of the water thus heated as boiler feed water, suitably for the high pressure waste heat boilers of a partial oxidation step or the shift step.

The methanol synthesis can be at any suitable pressure, for example in the range 20 to 400 bar abs. but is most conveniently in the range 30 to 120 bar abs. The steps of shift and $CO_2$ removal and also of preceding partial oxidation and purification are preferably at a pressure at least 90% of that of the synthesis, so as to require no compressor or at most the degree of compression afforded by a synthesis gas circulator.

The synthesis catalyst usually contains also zinc oxide and one or more further oxides, such as of chromium (our U.K. Pat. No. 1010871) or metals from Groups II–IV of the Periodic Table, especially aluminium (our U.K. Pat. 1159035) or possibly manganese or vanadium.

FIG. I is a flowsheet of a methanol synthesis plant with heat recovery and steam provision according to the invention;

FIG. II is a flowsheet of the stages of synthesis gas preparation for such a plant; and FIG. III is an alternative form of methanol synthesis unit for substitution in the FIG. I flowsheet.

The items of the flowsheets are numbered in the direction of gas flow.

In FIG. 1 a carbon monoxide stream, from which $CO_2$ and non-refractory sulphur compounds have been removed in stages to be described with respect to FIG. II, enters humidifying tower 10 at 40 and therein contacts in packing 42 a downward counter-current stream of hot water fed in at 44. The hot water has been heated in the stream of reacted methanol synthesis gas in heat exchanger 46, through which it has been circulated by pump 48. The cooled hot water leaves the bottom of the tower at 50, may undergo low grade heat recoveries (not shown) and receives a supply of warm make-up water at 52. It enters tower 60 (to be described) at 64 and therein picks up steam and is re-heated. It then is passed to pump 48 and exchanger 46 for further heating to provide the hot water stream fed at 44. The carbon monoxide stream, now saturated with water vapour, passes overhead from tower 10, is heated to shift inlet temperature in feed/effluent heat exchanger 54 and passed into shift reactor 56, where it reacts exothermally. The shifted hot gas is cooled in high pressure waste heat boiler 57, then in exchanger 54, cooled further in exchange with water in boiler feed water heater 58 and then finally cooled and largely freed of unreacted steam in de-humidifying tower 60. In tower 60 the gas flows counter-current in packing 62 to the downward stream of water fed in at 64. The gas leaving tower 60 overhead is passed to absorber 70 in which in packing 72 it contacts absorbent solution and is denuded of carbon dioxide and the $H_2S$ resulting from conversion of sulphur compounds in shift reactor 56. The loaded absorbent is run off at 76, passed to a regenerator (not shown) and returned to the absorber at 74.

The gas leaving tower 70 overhead is passed through final purifier 78, which typically contains a molecular sieve absorbent for residual sulphur compounds and water vapour, and thence to point 80 where it is mixed with a recycle stream of unreacted methanol synthesis gas. The mixed gas is pumped by circulator 82 through low grade heat exchanger 84 and the resulting warm gas is divided at 86 into a main feed stream and a quench stream. The main stream is heated to synthesis catalyst inlet temperature in exchanger 88 and fed to the inlet of synthesis reactor 90, which is of the single-bed quench type. The quench stream is passed to quench inlets 92, each of which feeds a sparger inside a catalyst-free perforated hollow bar constituting a mixing zone. The reacted synthesis gas at 270° C. is divided at 94, cooled in parallel heat exchangers 46 and 88 already mentioned, then re-united and cooled further in low grade heat exchanger 84 already mentioned. Its temperature is now too low for further worth while heat recovery and accordingly it is cooled at 96 with atmospheric air to below the dewpoint of methanol. The resulting mist is separated at 98 into a crude methanol bottoms stream passed out at 100 to distillation (not shown) and an overhead unreacted gas stream which is divided at 102 into a recycle stream passed to point 80 and a purge stream 104, which may if desired be heated and let down in a turbine to effect a further heat recovery.

In FIG. II tower 10 includes three packed regions 14, 30 and 42. A crude warm carbon monoxide stream (170° C., 60 bar abs.) from the water-scrubbing carbon removal stage of a partial oxidation plant enters at 12 and is cooled and largely freed of water vapour in packing 14 by counter-current contact with cold water fed in at 16. The cooled gas is led out at 18 to absorber 20 in which in packing 22 it contacts downward flowing absorbent liquid such as tetramethylene sulphone ("Sulfinol") and is freed of carbon dioxide and $H_2S$. The loaded absorbent is run off at 24 to a regenerator (not shown) and returned to absorber 20 at 26. The gas returns at 28 to the middle section of tower 10 and is warmed and humidified in packing 30 by warm water derived from the bottom section of tower 10 at 32 and pumped into the section at 36 by pump 34. Thus the water vapour and heat removed in the bottom section are returned to the gas in the middle section: note, however, that the cooling and drying take place only to the moderate extent possible in the presence of cold water. The warmed gas then leaves the middle section and enters the upper, main humidifying section by way of chimney-plate 40. The operation of this section has already been described in relation to FIG. I.

In FIG. III the synthesis reactor 90 contains catalyst in tubes 91 and the space about the tubes is filled with water. As the synthesis reaction proceeds, the exothermic heat is taken up by the water, which boils and circulates into and out of steam drum 93. Steam leaving drum 93 is passed to heat exchanger 47 in which it condenses and heats water fed in from pump 48 shown on FIG. I. The resulting condensate 95 is fed back to steam drum 93 and the heated water is fed at 44 into the humidifier 10 of FIG. I or FIG. II. If the water can be kept sufficiently pure and if corrosion-resistant materials of construction are used, the heat exchange at 47 can be direct.

The remaining items in FIG. III serve the same function as in FIG. II and need not be described further.

FIGS. I and II show typical temperatures in a preferred process for making 1 te $h^{-1}$ of methanol from a carbon monoxide stream delivered at 170° C., 55.7 bar abs. pressure at the rate of 131 kg mol $h^{-1}$ (wet), 120.8 kg mol $h^{-1}$ (dry) from a non-catalytic partial oxidation of heavy oil. The water feed rate at point 44 is 2.28 te $h^{-1}$ at 250° C. and 1.97 te $h^{-1}$ of water at 180° C. are passed out at 50 for recycle to the heater. In high pressure boiler 57 heat is recovered at the rate of 175,000 k cal $h^{-1}$.

In a corresponding process not according to the invention 0.98 te $h^{-1}$ of expensive high pressure steam (87 bar, 301° C.) is added to the carbon monoxide stream and only 168,000 k cal $h^{-1}$ of heat are recovered from the shift effluent.

I claim:

1. A process for producing methanol from a carbon monoxide stream which comprises the steps of
   (a) forming a gaseous mixture comprising carbon monoxide and steam;
   (b) reacting the mixture over a shift catalyst to produce a shifted gas comprising carbon monoxide, carbon dioxide and hydrogen;
   (c) removing any excess steam and at least part of the carbon dioxide from the shifted gas;
   (d) reacting the resulting gas over a copper-containing methanol synthesis catalyst at an outlet temperature under 300° C.; and
   (e) cooling the reacted synthesis gas and separating methanol from it: wherein said process further comprises the steps of
   (i) in step (e) transferring exothermic heat of synthesis into water under pressure; and
   (ii) in step (a) bringing the resulting hot water under pressure into direct heat exchange with the carbon monoxide stream, whereby to supply at least part of the steam of the gaseous mixture.

2. A process according to claim 1 in which the carbon monoxide stream to be heat exchanged in step (ii) is one made by partial oxidation of a carbonaceous feedstock followed by removal of by-product carbon and scrubbing with an absorbent liquid to remove at least $CO_2$ and $H_2S$.

3. A process according to claim 1 in which in step (i) exothermic heat of methanol synthesis is transferred into water by passing reacted gas leaving the synthesis catalyst through two parallel heat exchanges, the first of which heats synthesis gas to synthesis inlet temperature and the second of which heats water to a temperature in the range 200°–270° C.

4. A process according to claim 1 in which the outlet temperature of shift step (b) is in the range 350°–500° C.

5. A process according to claim 4 in which the shifted gas is cooled in a boiler generating steam at a pressure in the range 50 to 150 bar abs.

6. A process according to claim 1 in which water used as feed to step (i) is heated by direct heat exchange with the outlet gas from shift stage (c), whereby to remove steam from that gas.

7. A process according to claim 2 which comprises in step (a) producing a carbon monoxide stream containing byproduct carbon, $CO_2$, $H_2S$ and refractory sulphur compounds by partial oxidation of a sulphur-containing carbonaceous feed-stock, removing the by-product carbon, scrubbing the gas at a temperature in the range minus 10° to +100° C. with an absorbent selected from ethanolamine, potassium carbonate, tetra-methylene sulphone, propylene carbonate, N-methyl-2-pyrrolidone and dimethyl ether of polyethyleneglycol, whereby to remove $CO_2$ and $H_2S$ but not refractory sulphur compounds; and in step (b) by the action of the shift catalyst decomposing said refractory sulphur compounds with the formation of $H_2S$; and in step (c) removing $H_2S$ along with the $CO_2$ produced in the shift reaction of step (b).

8. A process according to claim 2 which comprises in step (a) producing a carbon monoxide stream containing byproduct carbon, $CO_2$, $H_2S$ and COS by partial oxidation of a sulfur-containing carbonaceous feedstock, removing the byproduct carbon, scrubbing the gas at a temperature in the range minus 10° to +100° C. with an absorbent selected from ethanolamine, potassium carbonate, tetramethylene sulphone, propylene carbonate, N-methyl-2-pyrrolidone and dimethyl ether of polyethyleneglycol, whereby to remove $CO_2$ and $H_2S$ but not COS compounds; and in step (b) by the action of the shift catalyst decomposing said COS with the formation of $H_2S$; and in step (c) removing $H_2S$ along with the $CO_2$ produced in the shift reaction of step (b).

9. A process according to claim 7 in which the carbon monoxide stream entering the direct heat exchange in step (ii) is at a temperature in the range 100°–180° C. and has been produced by the steps of partial oxidation of a sulphur-containing carbonaceous feedstock, scrubbing the resulting gas with water whereby to remove by-product carbon and produce a crude water vapour saturated gas at 150°–200° C., contacting the crude gas with water at 0°–100° C. whereby to produce a cooled gas and a warm water stream, treating the cooled gas with the said absorbent for $CO_2$ and $H_2S$, and contacting the treated gas with the warm water whereby to reheat it to 100°–180° C.

* * * * *